US00PP37161P2

(12) United States Plant Patent
Valstar

(10) Patent No.: US PP37,161 P2
(45) Date of Patent: Dec. 16, 2025

(54) ***CALATHEA* PLANT NAMED 'HGV23'**

(50) Latin Name: ***Calathea lietzei* e. morren**
Varietal Denomination: HGV23

(71) Applicant: Gebr. Valstar Beheer B.V., Maasland (NL)

(72) Inventor: Oscar Valstar, Maasland (NL)

(73) Assignee: Gebr. Valstar Beheer B.V., Maasland (NL)

( * ) Notice: Subject to any disclaimer, the term of this patent is extended or adjusted under 35 U.S.C. 154(b) by 0 days.

(21) Appl. No.: 19/288,552

(22) Filed: Aug. 1, 2025

(51) Int. Cl.

| | |
|---|---|
| ***A01H 5/00*** | (2018.01) |
| ***A01H 5/02*** | (2018.01) |
| ***A01H 5/12*** | (2018.01) |
| ***A01H 6/00*** | (2018.01) |

(52) U.S. Cl.
USPC ..... Plt./375
CPC ..... *A01H 6/00* (2018.05); *A01H 5/02* (2013.01); *A01H 5/12* (2013.01)

(58) Field of Classification Search
USPC ..... Plt./373, 375
See application file for complete search history.

(56) References Cited

U.S. PATENT DOCUMENTS

PP34,452 P2 * 7/2022 DeRoose ..... Plt./375

* cited by examiner

*Primary Examiner* — Karen M Redden
(74) *Attorney, Agent, or Firm* — Samuel R McCoy, Jr.

(57) ABSTRACT

'HGV23' is a new and distinctive variety of *Calathea* variety which is characterized by unique variegation and inflorescence. 'HGV23' exhibits a foliar variegation pattern of conspicuous bands radially extending from a yellow-green blotch in the central zone of the foliage transitioning to a combination of light and dark green with yellow green distally on the adaxial surface. Dark green mature abaxial foliar surfaces with variegation pattern consisting of broad blotches of color radially transitioning from green to greyed-purple. Alternating raceme inflorescence with floral bracts producing small translucent white and purple flowers. 'HGV23' has shown to express these characteristics consistently and stable from generation to generation.

3 Drawing Sheets

Latin name of the genus and species: The Latin name of the genus and species of the novel variety disclosed herein is *Calathea lietzei* E. Morren.

Variety denomination: The inventive variety of *Calathea* disclosed herein has been given the variety denomination 'HGV23'.

BACKGROUND OF THE INVENTION

Parentage: 'HGV23' originated as a naturally occurring, partial-plant mutation of an unnamed *Calathea lietzei* plant (not patented) which typifies the species. The claimed plant was discovered in March of 2023 at a commercial greenhouse in Maasland, Netherlands. The mutation was noted for its unique foliage coloration and was subsequently harvested from the parent plant, rooted in a nursery container, and grown to maturity to evaluate the distinctness and stability of the characteristics first observed. Upon confirmation of its distinctness and stability, the new *Calathea* plant was selected for commercialization and given the name 'HGV23' in August 2023.

Asexual Reproduction: Asexual reproduction of 'HGV23' through meristematic tissue culture was first performed in March of 2023 at a commercial greenhouse in Maasland, Netherlands. Five successive generations produced have shown that the unique features of the instant cultivar are stable and reproduced true to type.

SUMMARY OF THE INVENTION

The cultivar has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Calathea* cultivar 'HGV23'. These traits, in combination, distinguish 'HGV23' as a new and distinct cultivar.

1. *Calathea* 'HGV23' exhibits a foliar variegation pattern of conspicuous bands radially extending from a yellow-green blotch in the central zone of the foliage transitioning to green and yellow-green distally on the adaxial surface; and
2. *Calathea* 'HGV23' exhibits a dark green mature foliar abaxial surface with variegation patterns consisting of broad blotches of color radially transitioning from green to greyed-purple distally; and
3. *Calathea* 'HGV23' exhibits an alternating raceme inflorescence with floral bracts producing small translucent white and purple flowers.

BOTANICAL DESCRIPTION OF THE PLANT

Figure 1:
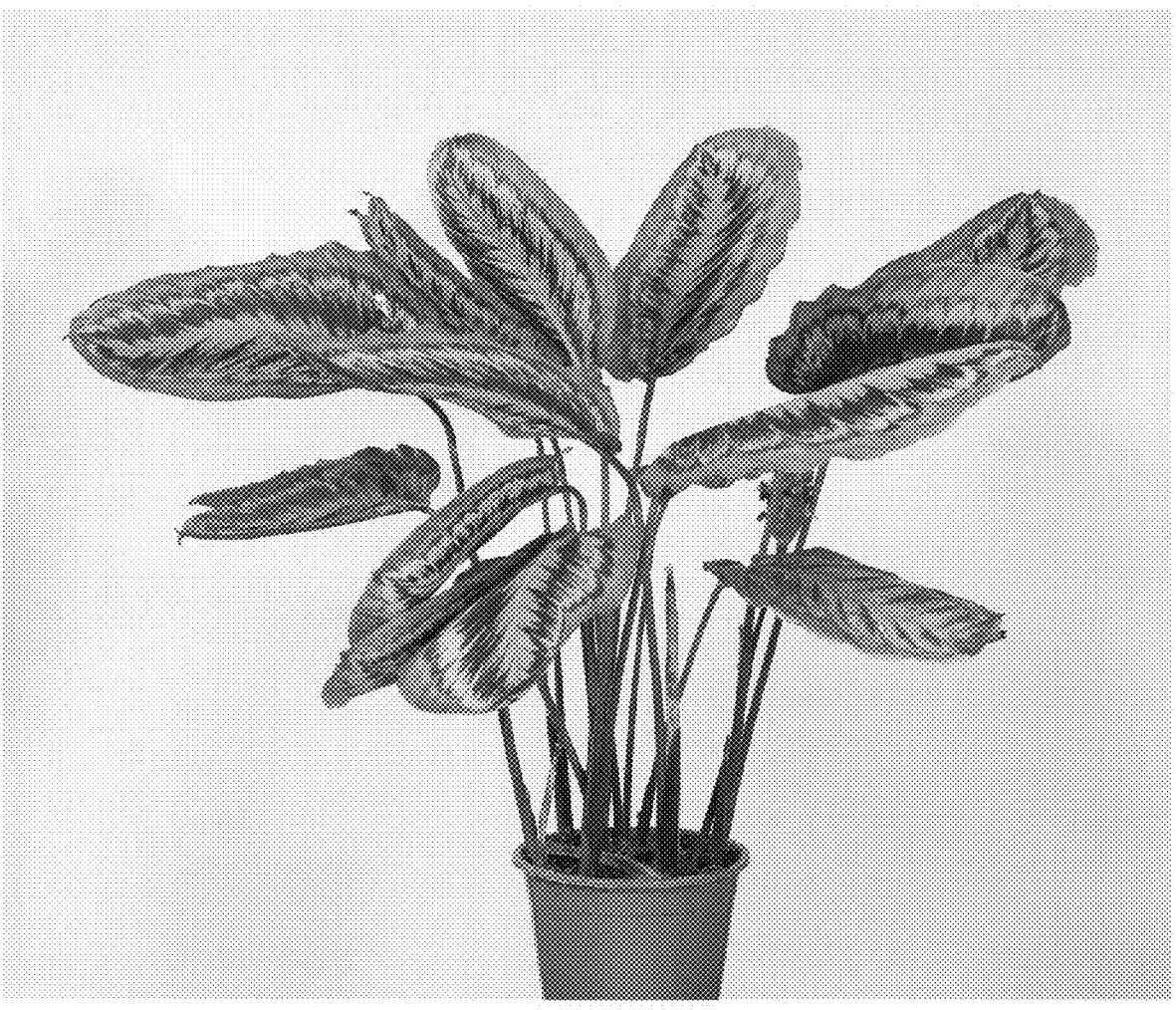
FIG. 1 shows, as nearly true as it is reasonably possible to make the same in color illustrations of this type, an exemplary 'HGV23' plant at 12-month-old, potted into a 19 cm nursery container, grown in a greenhouse in Maasland, the Netherlands.
Figure 2:
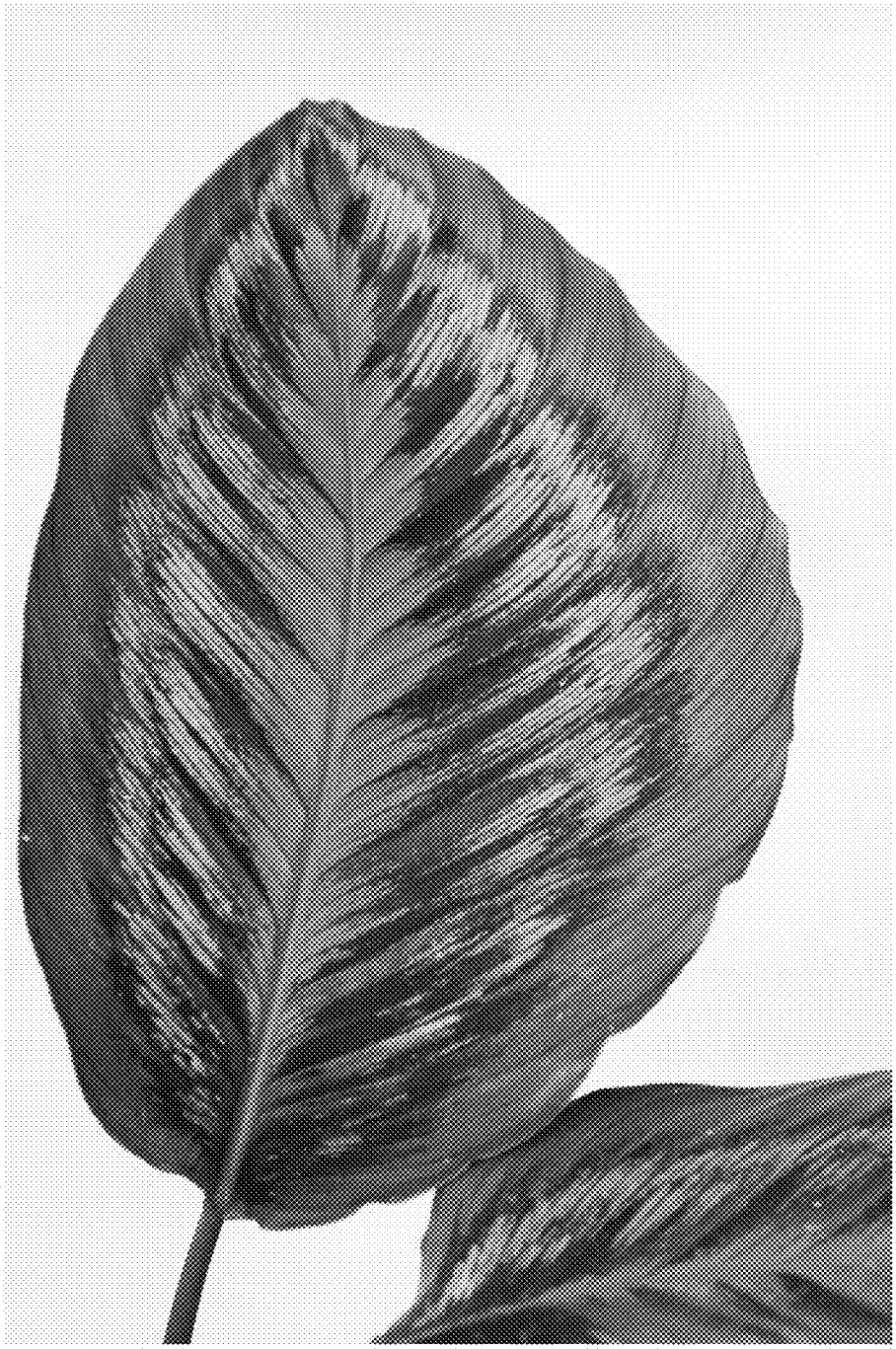
FIG. 2 shows, as nearly true as it is reasonably possible to make the same in color illustrations of this type, the typical mature foliage of 'HGV23'.
Figure 3:
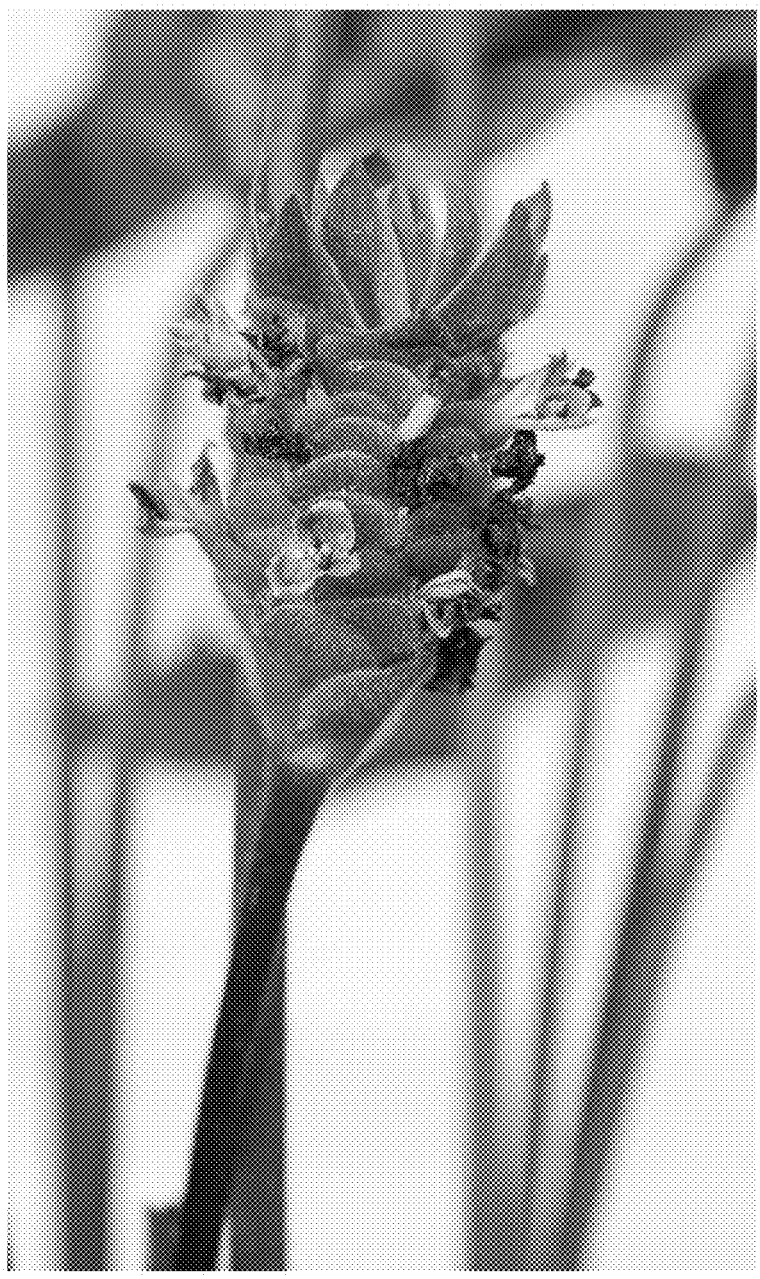
FIG. 3 shows, as nearly true as it is reasonably possible to make the same in color illustrations of this type, the typical inflorescence of a mature 'HGV23'.

The following is a detailed botanical description of a new and distinct variety of *Calathea* known as 'HGV23', based upon observations of plants, approximately 12-month-old from a rooted cutting, grown in 15 cm nursery container in a climate-controlled greenhouse in Maasland, the Netherlands. Observation data was recorded in March of 2024. Plants were produced using conventional greenhouse production protocols for *Calathea* sp. which consisted of growing under shade with regular overhead irrigation. No pest control measures were utilized, and no photoperiodic treatments or artificial light was given to the plants.

Those skilled in the art will appreciate that certain characteristics will vary with older or, conversely, with younger plants. 'HGV23' has not been observed under all possible environmental conditions. Where dimensions, sizes, colors, and other characteristics are given, it is to be understood that such measurements are approximations or averages set forth as accurately as practicable. The phenotype of the variety may differ from the descriptions set forth herein with variations in environmental, climactic, and cultural conditions. Color notations are based on *The Royal Horticultural Society Colour Chart*, The Royal Horticultural Society, London, 2019 Reprint.

A botanical description of 'HGV23' and comparisons with the parent and the most similar variety of common knowledge are provided below.

Plant description:

*Growth habit*.—Basally clump-forming, upright, flowering perennial.

*Plant profile*.—Broad flattened obovate.

*Height from soil level to the top of the foliar plane*.—59.0 cm.

*Height from soil level to the top of the floral plane*.—33.0 cm.

*Plant diameter*.—75.0 cm.

*Propagation*.—Mode of propagation — Meristematic tissue culture micropropagation. Time to initiate roots — Approximately 16 days to initiate roots at approximately 20 degrees Celsius. Time to produce a finished plant — Approximately 40 weeks to produce a marketable plant in a 15 cm nursery container.

*Environmental tolerances*.—USDA Zones 11 to 12; at least tolerant of temperatures as low as 8 degrees Celsius and up to 30 degrees Celsius. Moderate tolerance to rain inundation; moderate tolerance to wind. Low drought tolerance.

Root system:

*Branching habit*.—Rhizomatous with rhizomes bearing a moderately dense network of feeder roots.

*Distribution*.—Roots are shallow.

*Texture*.—Fibrous; non-fleshy.

*Color*.—Grey-brown, RHS 199D.

Stems:

*Branching characteristics*.—Basal foliage emerges directly from underground rhizomes; no lateral branching.

*Number of basal shoots*.—8.

Foliage:

*Arrangement*.—Alternate.

*Division*.—Simple.

*Attachment*.—Petiolate.

*Quantity of leaves per shoot*.—Average of 2.

*Quantity of shoots per plant*.—Average of 8.

*Quantity of leaves per plant*.—Approximately 15.

*Lamina*.—Shape — Broad elliptic to broad ovate. Apex — Abruptly acute. Base — Rounded to shallow truncate. Aspect — Predominantly concave, yet occasionally convex; margins occasional involute, particularly near the apex. Attitude — Leaves emerge in the same plane as the petiole yet mature to an approximate angle of 60 to 90 degrees relative to the petiole. Dimensions — 30.1 cm long and 19.3 cm wide, on average. Margin — Entire; moderate undulation. Texture and luster, adaxial surface — Smooth, glabrous, and moderately glossy. Texture and luster, abaxial surface — Smooth, glabrous, and matte. Color — Juvenile color, adaxial surface — Foliage exhibits a variegation pattern of conspicuous bands radially extending distally from a yellow-green blotch, nearest to a blend of RHS 145C and 150D, in the central zone of the foliage. Radiating away from the central blotch, towards the margins, is a series of irregular bands of varying color: a darker shade of yellow-green, nearest to a blend of RHS 144A and 146D; a broadly diffused band of light yellow-green, nearest to RHS 145C and 150D; and a thin band of yellow-green, RHS 146D. Broadly margined with yellow-green, nearest to RHS 144B; edged with a darker shade of yellow-green, nearest to RHS 144A. Juvenile color, abaxial surface — Foliage exhibits a variegation pattern of conspicuous bands radially extending distally from a yellow-green blotch, RHS 145D, in the central zone of the foliage. Radiating away from the central blotch, towards the margins, is a series of irregular bands of varying color: a greyed-orange, nearest to a blend of RHS 177A and 177B; a broadly diffused band of yellow-green, RHS 150D; and a thin band of greyed-orange to greyed-red, nearest to a blend of RHS 177A and 178A. Broadly margined with yellow-green, RHS 144A; edged darker with greyed-orange, nearest to a blend of RHS 177B and 177C. Mature color, adaxial surface — Foliage exhibits a variegation pattern of conspicuous bands radially extending distally from a yellow-green blotch, RHS 138B, in the central zone of the foliage. Radiating away from the central blotch, towards the margins, is a series of irregular bands of varying color: green, RHS 146D; a broadly diffused band of green to yellow-green, nearest to a blend of RHS 139A and 147A; and a thin band of green, nearest to a blend of RHS 138C and 139D. Broadly margined with green, RHS 139A and 138A; edged with a darker shade of green, nearest to RHS 143A. Mature color, abaxial surface — Foliage exhibits a variegation pattern of conspicuous bands radially extending distally from a green blotch, RHS N138C, in the central zone of the foliage. Radiating away from the central blotch, towards the margins, is a series of irregular bands of varying color: a greyed-purple, RHS N186C; a broadly diffused green, RHS N138C; and a thin band of greyed-purple, RHS 183C. Broadly margined with green, RHS N138B;

edged darker with greyed-purple, RHS 183C. Venation — Vein pattern — Pinnate. Vein color, adaxial surface — Midrib is colored yellow-green, nearest to RHS 148B, whereas the lateral veins are colored green, nearest to a combination of RHS NN137A and 139A. Vein color, abaxial surface — Midrib is colored yellow-green, nearest to RHS 151A, whereas the lateral veins are colored greyed-purple, nearest to RHS N186B.

*Petiole, including geniculum*.—Length — Approximately 35.9 cm. Width — Approximately 0.8 cm at the proximal end and 0.7 cm at the distal end. Strength — Medium. Texture — Densely packed with short strigose pubescence, averaging in length at 1.0 mm, colored greyed-orange, nearest to RHS 166C. Luster — Both the adaxial and abaxial surface of the petiole are slightly glossy. Color, adaxial surface — Yellow-green RHS 148A, fading to a different yellow-green towards the proximal end, RHS N148B. Color, abaxial surface — Yellow-green, RHS 152B.

*Petiole wings*.—Length — 9.5 cm. Width — 1.0 cm. Texture and luster, adaxial surface — Glabrous; glossy. Texture and luster, abaxial surface — Densely packed with short strigose pubescence, averaging in length at 1.0 mm; color almost indistinguishable from surrounding area but closest to greyed-orange RHS 165B. Matte. Color, adaxial surface — Yellow-green, nearest to HS N148A and RHS N148B. Color, abaxial surface — Yellow-green, RHS 152B.

*Geniculum*.—Length — Approximately 4.6 cm. Width — Approximately 0.7 cm. Color — Yellow-green, nearest to a blend of RHS 148A and 152A.

*Sheath*.—Shape — Lanceolate, folded around the base of the leaf. Apex — Shallow premorse. Base — Broad cuneate. Length — 13.5 cm. Width — Approximately 0.9 cm Texture — Glossy, densely packed with short strigose pubescence, averaging in length at 1.0 mm; color almost indistinguishable from surrounding area but closest to greyed-brown RHS 199B. Color — Greyed-brown, nearest to RHS N199A.

Inflorescence:

*Habit*.—Single alternate raceme, bracts supporting 3-flowered clusters.

*Dimensions*.—7.1 cm long and 5.0 cm wide.

*Natural flowering season*.—Late winter to summer.

*Time to flower or response time*.—10 weeks after flowering, on average.

*Quantity of open flowers per inflorescence*.—30, on average.

*Quantity of open flowers per plant*.—30, on average.

*Quantity of flower buds per plant*.—120, on average.

*Quantity of flowers and flower buds per plant*.—150, on average.

*Peduncles*.—Length — Average of 31.4 cm. Diameter — Average of 0.55 cm. Angle — Near vertical, average angle to stem is 90 degrees. Strength — Moderately strong. Texture — Moderately to densely packed with short strigose pubescence; hairs are an average length of 1.0 mm; colored greyed-brown, color almost indistinguishable from surrounding area but closest to RHS 199C and RHS 199D. Luster — Moderately glossy. Color — Greyed-brown, RHS N199B.

Flower buds:

*Shape*.—Lanceolate.

*Length*.—1.9 cm.

*Diameter*.—0.5 cm.

*Texture*.—Glabrous, smooth.

*Luster*.—Glossy.

*Color*.—The apex of the bud is yellow-green RHS 144B; fading distally to yellow- green, RHS 150D.

Flower:

*Shape, type*.—Asymmetrical, consisting of 3 petals and 3 sepals.

*Flowering habit*.—Low flowering.

*Aspect*.—Upright to outward.

*Flower longevity on plant*.—Approximately two days.

*Persistent or self-cleaning*.—Persistent.

*Fragrance*.—Non-fragrant.

*Diameter*.—0.8 cm.

*Depth*.—2.4 cm.

*Calyx*.—Shape — Rotate. Length — 1.1 cm. Diameter — 0.4 cm.

*Sepals*.—Arrangement — Rotate. Quantity — 3 unfused sepals. Shape — Lanceolate. Aspect — Slightly concave. Dimensions — 1.1 cm long and 0.3 cm wide. Apex — Acute. Base — Broad cuneate. Margin — Entire; no undulation. Texture and luster, upper surface — Smooth, glabrous, and glossy. Texture and luster, lower surface — Smooth, glabrous, and glossy.

*Color*.—When opening, upper surface — Translucent white, nearest to RHS N155B. When opening, lower surface — Translucent white, nearest to RHS N155B. Fully opened, upper surface — Translucent white, nearest to RHS 157D. Fully opened, lower surface — Translucent green-white, nearest to RHS 157D.

*Petals*.—Quantity — Three. Arrangement — Rotate; arranged in a single whorl of adenately fused petals. Length — Labium on average is 2.4 cm. Width — 0.45 cm. Shape — Obovate. Apex — Obtuse. Base — Fused to reproductive organs. Margin — Entire. Texture, upper surface — Smooth, glabrous, non-rugose, and matte. Texture, lower surface — Smooth, glabrous, non-rugose and very slightly glossy.

*Petal color*.—When opening, upper surface — Labium is purple, RHS 77D. Veins are a purple with a radial blotch distally from the base of the petal, nearest to RHS 77B; margins are tipped with violet, RHS 85C. The lateral petals are translucent violet, RHS 85D; margins edged with a combination of RHS 77B and RHS 77C. When opening, lower surface — Labium is purple, RHS 77C. The lateral petals are translucent green-white, RHS 157D. Fully opened, upper surface — Labium is purple, RHS 77D. Veins are purple with a radial blotch distally from the base of the petal, nearest to RHS 77B; margins are tipped with violet, RHS 85C. The lateral petals are translucent violet, RHS 85D; margins edged with a combination of RHS 77B and RHS 77C. Fully opened, lower surface — Labium is purple, RHS 77C. The lateral petals are translucent green-white, RHS 157D When faded, upper surface — Labium is purple, RHS N77C. The lateral petals are translucent green-white, RHS 157D. When faded, upper surface — Labium is purple, RHS N77C. The lateral petals are translucent green-white, RHS 157D.

*Flower throat color*.—Green-white, RHS 157A.

*Flower tube color*.—Green-white, nearest to RHS 157D.

Floral bracts:

*Lower bracts*.—Position — Lower bracts are present at the base of each cluster of 3 flowers, 50 on average. Shape — Reniform. Aspect — Concave. Length — 1.8 cm. Width — 2.3 cm. Apex — Emarginate Base — Cuneate. Margins — Entire. Color, adaxial surface — Yellow-green, RHS 144A; margins and tip of the lower bracts fade yellow-green, closest to RHS 145A. Color, abaxial surface — Green, RHS 143B margins and tip of the lower bracts fade to yellow-green closest to 145A. Texture, adaxial surface — Smooth, glabrous, non-rugose and glossy. Texture, abaxial surface — Non-rugose, slightly glossy and densely packed with soft strigose pubescence, hairs are 1.0 mm in length, nearly indistinguishable from surrounding area; to be seen as greyed-orange, RHS 165C.

*Upper bracts*.—Position — Upper bracts sit above the flower clusters on top of the inflorescence, on average 15 upper bracts are present. Shape — Ovate to elliptic. Aspect — Slightly carinate. Length — 3.2 cm. Width — 1.6 cm. Apex — Acute Base — Cuneate. Margins — Entire. Color, adaxial and abaxial surfaces — The upper surface is green, RHS 143A; margins of the lower bracts fade yellow-green, closest to RHS 145D. Abaxial surfaces have an over-tone of greyed-purple, RHS 183D. Texture, adaxial surface — Smooth, glabrous, non-rugose and glossy. Texture, abaxial surface — Non-rugose, matte and densely packed with soft strigose pubescence, hairs are 0.75 mm in length, nearly indistinguishable from surrounding area; to be seen as greyed-orange, RHS 165D.

Reproductive organs:

*Androecium*.—Stamens — Quantity — One. Anthers — Shape — Narrow oblong. Dimensions — 0.5 cm long and 0.1 cm wide. Color — Greyed-purple, RHS N187D. Filaments — Length — 1.5 cm. Color — White, RHS 155C. Amount of Pollen — Sparse. Pollen color — White, RHS NN155A.

*Gynoecium*.—Pistil — Quantity — One. Length — 2.3 cm. Style — Length — 2.0 cm. Color — White, RHS 155C. Stigma — Shape — Hooded. Diameter — 0.1 cm. Color — Greyed-purple, RHS N187B. Ovary Color — White, RHS 155C.

Seed and fruit: No seeds or fruit have been detected.

COMPARISONS WITH THE PARENT PLANT AND CLOSEST KNOWN COMPARATOR

Plants of the new cultivar 'HGV23' differ from its parent and closest known comparator, an unnamed *Calathea lietzei* E. Morren (not patented), by the characteristics described in Table 1.

TABLE 1

Differences Between 'HGV23' and The Parent Plant

| Characteristic | 'HGV23' | The Parent Plant |
|---|---|---|
| Leaf shape | Broad elliptic broad ovate with an abruptly acute apex. | Narrower than 'HGV23' with a more apiculate apex. |
| Leaf texture | Moderately glossy. | Slightly glossy. |
| Vein color prominence | Midrib and lateral venation coloration has more pronounced contrast with the surrounding laminar surface causing it to be more visible than the parent plant. | Midrib and lateral venation coloration blends in with surrounding laminar surface. |
| General coloration of leaves | Daker green than the parent plant. | Lighter green and yellow-green than 'HGV23'. |
| Expression of variegation | Foliage exhibits a variegation pattern of conspicuous bands radially extending distally from the central zone of the foliage. | Widely striated block sections of variegation that are a lighter yellow-green and green than the colors visible on 'HGV23'. |
| General shape and pattern of variegation | Pinnate and ovate outline of variegation on the laminar surface. | Lanceolate outline of variegation on the laminar surface. |

COMPARISONS WITH THE CLOSEST KNOWN COMPARATOR

Plants of the new cultivar 'HGV23' may be distinguished from the *Calathea* variety 'Mysty' (U.S. Plant Pat. No. 34,452) by the combination of characteristics described in Table 2.

TABLE 2

Comparisons Between 'HGV23' and 'Mysty'

| Characteristic | 'HGV23' | 'Mysty' |
|---|---|---|
| Presence of inflorescence | Single alternate raceme supporting on average 30 asymmetrical shaped translucent white and violet tinged flowers. | Upright terminal compound spike supporting on average 468 flowers corolla cruciform shaped white and purple tinged flowers. |
| Plant height and diameter | Taller and less outreaching than 'Mysty'. 59.0 cm in height and 75.0 cm in diameter, on average. | Shorter and more outreaching than 'HGV23'. 42.5 cm in height and 79.6 cm in diameter, on average. |
| Leaf size and shape. | Larger than 'Mysty', broad elliptic to broad ovate in shape and on average 30.1 cm in length and 19.3 cm in width. | Smaller than 'HGV23', broad elliptic to broad obovate in shape and on average 23.2 cm in length and 17.7 cm in width. |
| Variegation expression. | Foliage exhibits a variegation pattern of conspicuous bands radially extending distally from the central zone of the foliage. | Foliage exhibits a variegation pattern of conspicuous bands thicker than 'HGV23' radially extending distally from the central zone of the foliage. |

TABLE 2-continued

Comparisons Between 'HGV23' and 'Mysty'

| Characteristic | 'HGV23' | 'Mysty' |
|---|---|---|
| General coloration of the mature foliage; adaxial surface. | Dark green lamina with light green irregular outlines of ovate shapes surrounding the green center, feathering towards the margin which is green outlined in a darker green. | Darker green laminas than 'HGV23' with greyed green irregular outlines of ovate shapes surrounding the green center, feathering towards the margin with a darker green and a pink tinge along the cream white portion of the variegation. |
| General coloration of the mature foliage; abaxial surface. | Dark green lamina with dark purple irregular outlines of ovate shapes surrounding the green center, feathering towards the margin which is green outlined in a dark purple. | Bright pink-purple lamina with dark green irregularly outlined bands striating the surface of the lamina. |
| Venation color, adaxial surface. | The midrib is yellow-green, and the lateral veins are green. | Yellow green with a purple tint on the midrib. |
| Venation color, abaxial surface. | The midrib is yellow-green, and the lateral veins are greyed-purple. | Purple. |

That which is claimed is:

1. A new and distinct variety of *Calathea* plant named 'HGV23', substantially as described and illustrated herein.

* * * * *